United States Patent [19]

Stevens et al.

[11] 4,350,644
[45] Sep. 21, 1982

[54] ISOPROPYLBENZENE DERIVATIVES

[75] Inventors: John Stevens; Stephen Newman, both of Harlow, England

[73] Assignee: Minnesota Mining and Manufacturing Company, St. Paul, Minn.

[21] Appl. No.: 38,699

[22] Filed: May 14, 1979

[30] Foreign Application Priority Data

May 15, 1978 [GB] United Kingdom ............... 19554/78

[51] Int. Cl.³ ......................................... C07C 143/02
[52] U.S. Cl. .......................... 260/501.15; 260/501.16; 260/501.21
[58] Field of Search ................... 260/501.15, 501.16, 260/501.21

[56] References Cited

FOREIGN PATENT DOCUMENTS 1966931 5/1975 Fed. Rep. of Germany ....................... 260/501.21
51-48621 4/1976 Japan .

Primary Examiner—Robert Gerstl
Attorney, Agent, or Firm—Cruzan Alexander; Donald M. Sell; Mark A. Litman

[57] ABSTRACT

Isopropylbenzene derivatives having the general formula:

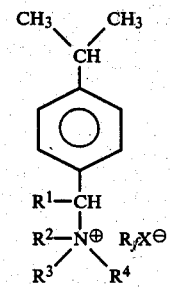

in which:
  $R^1$ to $R^4$ independently represent a hydrogen atom or a lower alkyl group having up to 4 carbon atoms,
  $X^\ominus$ represents $COO^\ominus$ or $SO_3^\ominus$, and
  $R_f$ represents a fluorinated organic radical.

The compounds may be applied to surfaces liable to be or become negatively charged to suppress spark discharges from such surfaces. Those compounds in which at least two of $R^2$, $R^3$ and $R^4$ are alkyl, are particularly useful in the top coat of photographic films to eliminate marks caused by spark discharges.

10 Claims, No Drawings

ISOPROPYLBENZENE DERIVATIVES

This invention relates to isopropylbenzene derivatives and to their preparation.

Copending British Patent Application No. 19554/78 discloses a method of suppressing spark discharges from a surface liable to be or become negatively charged, in which the surface is treated with an isopropylbenzene carrying a substituent with a Hammett $\sigma_p$ constant of from $-0.17$ to $+0.82$ in the 2- or 4- position relative to the isopropyl group or a substituent with a Hammett $\sigma_m$ constant of from 0.0 to $+0.88$ in the 3-position relative to the isopropyl group.

Unexpectedly, surfaces treated with such an isopropylbenzene derivative have a reduced tendency to spark discharge when they are carrying a negative triboelectric charge. The treatment of a surface with an isopropylbenzene derivative does not prevent a negative charge from forming on the surface nor discharge a negative charge formed on that surface. Instead it suppresses spark discharges from that surface.

The above method has particular application to reducing spark discharges from photographic films and in particular to radiographic photographic films. An isopropylbenzene derivative coated on the surface of the film reduces static marks arising from contact electrification.

The requirements for an isopropylbenzene derivative for use with a film is that it must be capable of being coated with the protective gelatin top coat and be capable of preventing exposure of the film by the spark discharge of the static charge generated by handling under low humidity conditions. The derivative must not degrade the photographic properties of the film. The derivative must be effective at relative humidity of 40% or less, above this humidity the gelatin is sufficiently hygroscopic to provide a conductive layer on the surface of the film and prevent the build up of a static charge.

Furthermore the isopropylbenzene derivative must be soluble at low concentrations in the gelatin solution used for the top coat. The derivative must be compatible with the gelatin and the hardening agents and should possess surfactant properties which confer a low surface tension on the gelatin solution and allow the derivative to concentrate at the surface of the coating. Finally, the isopropylbenzene derivative should confer a negative charging characteristic to the gelatin surface since spark discharges can only be suppressed from negatively charged surfaces.

It is an object of the present invention to provide isopropylbenzene derivatives which may be used to reduce spark discharges from photographic films.

Therefore according to the present invention there is provided an isopropylbenzene having the general formula:

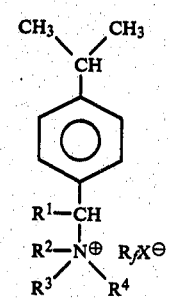

in which
$R^1$ to $R^4$ independently represent a hydrogen atom or a lower alkyl group having up to 4 carbon atoms,
$X^\ominus$ represents $COO^\ominus$ or $SO_3^\ominus$, and
$R_f$ represents a fluorinated organic radical (as defined herein).

The fluorinated organic radical $R_f$ is defined as a radical which is a saturated, aliphatic radical having up to 20 and preferably at least 3 carbon atoms, the skeletal chain of which may be straight, branched or if sufficiently large cycloaliphatic, the skeletal chain may be interrupted by divalent oxygen or trivalent nitrogen atoms bonded only to carbon atoms provided the radical does not contain more than one heteroatom, i.e. nitrogen or oxygen, for every two carbon atoms in the skeletal chain the radical being fully fluorinated with the exception that it may contain hydrogen or chlorine atoms as substituents provided that no more than one atom of either is present in the radical for each carbon atom. Preferably, the fluoraliphatic radical is a perfluoroalkyl radical having a skeletal chain that is straight or branched.

The variation of surfactant power with the size of the $R_f$ chain is discussed in Kirk-Othmer, Encyclopedia of Chemical Technoloyy, 2nd edition, Volume 9, pages 724 to 726, to which reference is made. However, in view of the properties of ionic conduction and negative electrification conferred by the fluorocarbon acid $R_f$ radicals having 1 and 2 carbon atoms are also useful.

Examples of suitable $R_fX^\ominus$ groups include: perfluoro-octyl sulphonate and carboxylate, and perfluoropentyl sulphonate and carboxylate.

The compounds of the invention are compatible with gelatin and exhibit good spark suppression in photographic film. Those compounds in which two or more of $R^2$, $R^3$ and $R^4$ are hydrogen react with formaldehyde and therefore may not be used with formaldehyde hardened film. However, they exhibit good spark suppression effects with films hardened by other agents, e.g. chrome alum. Those compounds in which at least two of $R^2$, $R^3$ and $R^4$ are lower alkyl may be used with formaldehyde hardened film and are preferred. The compounds of the invention may also be applied as surface coatings from solution and in other surface coating compositions as disclosed in copending British Patent Application No. 19554/78.

The compounds of the present invention may be prepared according to the following reaction scheme:

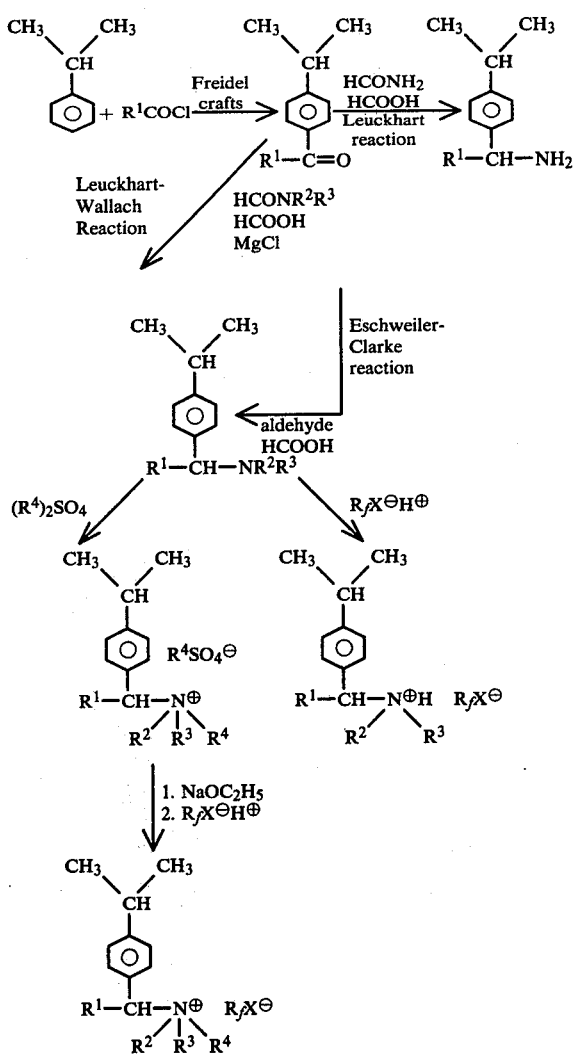

The Leuckhart reaction and Eschweiler-Clarke reactions are disclosed in Organic Reactions, Volume 5, 1960, Wiley, and the Leuckhart-Wallach reaction in Name Index of Organic Reactions, Gowan and Wheeler, Longmans, 1960.

The acylation of isopropylbenzene is preferably carried out in the presence of aluminium chloride as catalyst. The remaining steps in the reaction scheme are conducted according to conventional techniques.

The invention will now be illustrated by the following Examples.

EXAMPLE 1

Preparation of 1-(4-isopropylphenyl)ethyl ammonium perfluoro-octyl sulphonate

Formamide (78 g) was heated to reflux at 205° C. to 208° C. in a flask fitted with a dropping funnel and a Dean and Stark apparatus. It is essential that the formamide remains clear at reflux, if dark brown drops are formed in the condensate, the material must be purified.

A mixture of 4-isopropylacetophenone (81 g) and formic acid (19 ml 98/100%) was added dropwise to the boiling formamide. The liquid foamed vigorously as the drops entered the formamide and two layers formed in the Dean and Stark apparatus. The upper layer was mainly the ketone and was allowed to run back into the reaction mixture. The lower layer was run off for the first 15 ml and then allowed to run back also. The reaction solution become golden yellow and the internal temperature fell to 180° C. as the addition proceeded. The addition was made over 1 hour and the reaction mixture was heated at an internal temperature of 185° C. for a further 4 hours. On cooling the reaction mixture remained homogeneous, if the cold solution separates into two phases, the reaction is not completed.

The reaction mixture was poured into 50% hydrochloric acid (300 ml). The formamide hydrolysed rapidly and an oil was precipitated. Ethanol (50 ml) was added to obtain a clear solution and this solution was boiled under reflux for 6 hours. After cooling, this solution was basified with 40% sodium hydroxide solution and a yellow oil was precipitated. When cool, the oil was extracted with ether and the ether solution was separated and dried over magnesium sulphate. Evaporation of the ether solution gave a yellow oil which was distilled at the water pump to give 1-(4-isopropylphenyl)ethylamine as a colourless oil, boiling point 106° to 108° C./12 mm (reported boiling point 111° to 113° C./15 mm) 65%

NMR data: $1.17\delta$ (6H) doublet (J=7 Hz); $1.20\delta$ (3H) doublet (J=7 Hz); $1.29\delta$ (2H) singlet; $2.78\delta$ (1H) multiplet (J=7 Hz); $3.89\delta$ (1H) quartet (J=7 Hz); $7.10\delta$ (4H) doublet.

The perfluoro-octylsulphonate salt was prepared by mixing a solution of 1-(4-isopropylphenyl)ethylamine (16.1 g) in ethanol (20 ml) with a solution of perfluoro-octylsulphonic acid (50 ml). The solution was evaporated to dryness and the residue was recrystallised from chloroform as soft colourless plates of 1-(4-isopropylphenyl) ethyl ammonium perfluoro-octyl sulphonate, melting point 158° C.(d). (Found: C 34.3; H 2.5; N 2.2%. $C_{19}H_{18}F_{17}NO_3S$ requires: C 34.40; H 2.73; N 2.11%).

EXAMPLE 2

Preparation of N-methyl-1-(4-isopropylphenyl) ethylammonium perfluoro-octyl sulphonate A suspension of 1-(4-isopropylphenyl) ethylamine (81 g) was stirred vigorously in a solution of sodium hydroxide (50 g) in water (250 ml) at room temperature. Dimethyl sulphate (64 g) was added dropwise to the stirred suspension over a period of 1 hour. The suspension was stored in a refrigerator overnight and three layers were formed. The top layer of organic material was extracted with ether and the ether solution was separated and dried over anhydrous magnesium sulphate. The ether was evaporated under reduced pressure to give a yellow oil which was distilled at a water pump to give N-methyl-1-(4-isopropylphenyl) ethylamine (61 g, 69%) colourless oil, boiling point 112° to 114° C./20 mm.

The perfluoro-octyl sulphonate salt was prepared by mixing a solution of N-methyl-1-(4-isopropylphenyl) ethylamine (17.6 g) in ethanol (20 ml) with a solution of perfluoro-octylsulphonic acid (50 g) in ethanol (150 ml). The ethanol solution was evaporated under reduced pressure and the solid residue was recrystallised from chloroform as soft colourless plates of N-methyl-1-(4-isopropylphenyl) ethylammonium perfluoro-octylsulphonate (60 g). (Found: C 33.05; H 2.43; N 2.09%. $C_{20}H_{20}F_{17}NO_3S$ requires: C 35.4; H 2.98; N 2.07%).

EXAMPLE 3

Preparation of N-N-dimethyl-1-(4-isopropylphenyl) ethyl ammonium perfluoro-octyl sulphonate 1-(4-isopropylphenyl) ethylamine (40 g) was added cautiously with cooling to formic acid (55 g, 98%). Formaldehyde solution (125 ml, 32%) was added and the solution was heated on a steam bath under reflux for 16 hours. The solution bubbled vigorously at first but the evolution of gas was not maintained. After cooling, hydrochloric acid (50 ml 35% w/v) was added and the solution was evaporated to a syrup to remove formaldehyde and formic acid. The residue was made alkaline with sodium hydroxide solution and the organic material was extracted with ether. After drying the ether was evaporated to leave a brown oil which was distilled at the water pump to give N-N-dimethyl-1-(4-isopropylphenyl) ethylamine as a colourless oil, boiling point 124° C. 126° C./20 mm. (30 g, 70%).

NMR data 5% solution in dueterochloroform. 1.2$\delta$ (6H) doublet (J=7 Hz), 1.3$\delta$ (3H) doublet (J=7 Hz), 2.15$\delta$ (6H) singlet, 2.83$\delta$ (1) multiplet (J=7 Hz), 3.7$\delta$ (1H) multiplet (J=7 Hz), 7.1$\delta$ (4H) singlet.

The same compound was obtained by the methylation of N-methyl-1-(4-isopropylphenyl) ethylamine by heating with formic acid and formaldehyde on a steam bath for 6 hours (Yield 74%)

The perfluoro-octyl sulphonate salt was prepared by mixing a solution of N,N-dimethyl-1-(4-isopropylphenyl) ethylamine (19.0 g) in ethanol (20 ml) with a solution of perfluoro-octyl sulphonic acid (50 g) in ethanol (150 ml). The ethanol solution was evaporated under reduced pressure and the solid residue was recrystallised from chloroform as colourless plates of N,N-dimethyl-1-(4-isopropylphenyl) ethylammonium perfluoro-octyl sulphonate (65 g), melting point 65° C. (Found: C 36.08; H 2.72; N 2.21%. $C_{21}H_{22}F_{17}NO_3S$ requires: C 36.48; H 3.21; N 2.00%.).

EXAMPLE 4

Preparation of N,N,N-trimethyl-1-(4-isopropylphenyl) ethylammonium perfluoro-octyl sulphonate Dimethyl sulphate (25.2 g) in dry ether (100 ml) was added slowly to a stirred, water cooled solution of N,N-dimethyl-1-(4-isopropylphenyl) ethylamine (19.0 g) in dry ether over a period of 30 minutes. The reaction proceeded smoothly and a viscous oil formed as droplets in the ether. The stirring was stopped and the oil collected at the bottom of the flask allowing the ether to be decanted. The oil crystallised on standing. This product was dissolved in dry ethanol (50 ml) and added to a solution of sodium ethoxide (2.3 g of sodium) in ethanol (100 ml). The ethanol solution was stored at 0° C. overnight and a deposit of sodium methosulphate formed slowly. The deposite was filtered off and perfluoro-octyl sulphonic acid (50 g) in ethanol was added to the filtrate. The solution was evaporated to dryness and the residue recrystallised from chloroform after standing at 0° C. overnight. This gave colourless plates of N,N,N-trimethyl-1-(4-isopropylphenyl) ethylammonium perfluoro-octyl sulphonate. (62.3 g, 88%.) (Found: C 37.4; H 4.1; N 2.3%. $C_{22}H_{24}F_{17}NO_3S$ requires: C 37.46; H 3.43; N 1.99%).

EXAMPLE 5

Preparation of 1-(4-isopropylphenyl) ethylammonium perfluoro-octyl sulphonate

A solution of (4-isopropylphenyl) ethylamine (16.3 g) in acetone (50 ml) was added slowly to a vigorously stirred suspension of perfluoro-octyl sulphonyl fluoride (50.3 g) in acetone (100 ml) and triethylamine (10.1 g). The temperature rose to 35° C. and was maintained at this by controlling the rate of addition. The reaction mixture became clear as the reaction proceeded and became light brown. The solution was stirred for a further 1 hour before evaporating to dryness. The residue was washed with water and the organic residue was extracted with ether (200 ml). The ether layer was dried carefully with magnesium sulphate and evaporated on a rotary film evaporator to a brown syrup. Chloroform (100 ml) was added and the solution was evaporated at atmospheric pressure to a pot temperature of 63° C. After storing at 0° C. overnight the product cyrstallised as yellow needles. Recrystallised from toluene with charcoaling as colourless fluffy crystals of 1-(4-isopropylphenyl) ethylammonium perfluoro-octyl sulphonate, melting point 158° C. (38 g, 59%).

NMR data for 5% solution in DMSO (d$_6$) 1.21$\delta$ (6H) doublet (J=7 Hz); 1.51$\delta$ (3H) doublet (J=7 Hz); 2.9$\delta$ (1H) multiplet (J=7 Hz); 4.4$\delta$ (1H) multiplet (J=7 Hz); 7.34$\delta$ (4H) singlet; 8.15$\delta$ (3H) broad peak [with CF$_3$COOH].

It was initially believed that the compound prepared was N-[1-(4-isopropylphenyl)ethyl]perfluoro-octyl sulphonamide. However, analysis has now proved the compound to be a sulphonic acid salt. It is apparent that during the reaction a molecule of water was included. The water could have been provided from two sources:

(1) That the acetone was normal laboratory undried solvent which necessarily contains a few percent water. This would be sufficient to have hydrolysed the perfluoro-octyl sulphonyl fluoride to acid particularly in the presence of triethylamine.

(2) The water wash of the assumed sulphonamide would perhaps hydrolyse the compound to the sulphonic acid salt.

It is believed that (1) is the probable explanation for the formation of the acid salt.

The following Table 1 reports the data of compounds in accordance with the invention prepared according to Examples 1 to 4 or by analogous methods. In each compound $R_fX^\ominus$ was $C_8F_{17}SO_3$ with the exception of that marked (*) in which $R_fX^\ominus$ was $C_5F_{11}CO_2^\ominus$.

TABLE 1

| R$^1$ | R$^2$ | R$^3$ | R$^4$ | Melting point °C. | Theoretical C | H | N | Found % C | H | N |
|---|---|---|---|---|---|---|---|---|---|---|
| CH$_3$ | H | H | H | 158 | 34.40 | 2.73 | 2.11 | 34.30 | 2.5 | 2.2 |
| CH$_3$ | H | H | CH$_3$ | — | 35.42 | 2.98 | 2.07 | 33.05 | 2.43 | 2.09 |
| CH$_3$ | H | CH$_3$ | CH$_3$ | 73 | 36.48 | 3.21 | 2.00 | 37.19 | 3.37 | 2.14 |
| CH$_3$ | CH$_3$ | CH$_3$ | CH$_3$ | — | 37.46 | 3.43 | 1.99 | 37.4 | 4.1 | 2.3 |
| H | H | H | CH$_3$ | 113 | 34.40 | 2.73 | 2.11 | 35.84 | 2.44 | 2.34 |
| H | H | CH$_3$ | CH$_3$ | 111 | 35.42 | 2.98 | 2.07 | 35.84 | 2.52 | 2.21 |
| CH$_3$ | C$_2$H$_5$ | H | H |  | 37.01 | 3.23 | 2.06 | 38.35 | 3.33 | 2.19 |
| C$_3$H$_7$ | H | H | H | 126 | 36.47 | 3.18 | 2.03 | 36.10 | 2.82 | 2.10 |
| *CH$_3$ | H | H | H |  | 42.76 | 3.77 | 2.93 | 43.96 | 3.57 | 2.92 |

EXAMPLE 6

The spark suppression properties of compounds of the invention were tested in a gelatin top coat applied to a photographic film.

The apparatus used to examine the charging characteristics and incidence of spark discharges consisted of a driven earthed stainless steel roller in contact with a spring loaded non-metallic roller. A sheet of material was passed between the rollers and collected in a tray. The charge on the surface of the material was detected by an electrometer probe. The surface of the non-metalilc roller can be modified by wrapping a sheet of material round it so that the surface.

In contact with the material under examination can present a different work function. The detection and recording of spark discharges, was measured using a sheet of photographic film possessing a high sensitivity to blue light. Each piece of film was then passed between the rollers in a darkroom with an appropriate safelight, and then developed and fixed in a conventional manner. Heavy black marks were found on some sheets due to exposure of the light sensitive material by the light emitted during an electrical discharge. It was found that the polarity of the static charge induced on the film during the rolling process was distinguished by the type of marking. A negative static potential on the surface of the photographic film gave rise to sharp dense images exactly analogous to a picture of a lightning flash. A positive static potential on the surface of the photographic film gave diffuse formless images clearly differentiated from the marks due to discharge at a negative charged surface.

The marks visible on each film were visually graded according to the scale 0 to ±5. The zero value was accorded to films with no marks and 5 to a film bearing many marks rendering the film unsuitable for use. A positive sign represents marks attributed to positive static potential and a negative sign to marks attributed to negative static potential.

The following Table 2 reports the results of the tests conducted by rolling the film at 25% relative humidity with the spark suppression additives in the top coat. Compounds of the invention were compared with a known compound used for the reduction of static in photographic films as disclosed in U.S. Pat. No. 3,850,642.

TABLE 2

| Additive | Quantity (ml) of 4% aqueous solution of additive per 100 g of top coat gel | Static marking |
|---|---|---|
| (Comparison) $(CH_3)_3\overset{\oplus}{N}(CH_2)_3\underset{H}{N}SO_2C_8F_{17}Cl^{\ominus}$ | 3 | −4 |
| 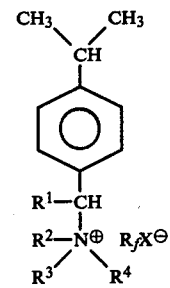 (with $C_8F_{17}SO_3^{\ominus}$ and $\overset{\oplus}{N}(CH_3)_2 H$) | 1 | −4 |
|  | 3 | −3 |
|  | 10 | 0 |
|  | 30 | 0 |
|  | 100 | −2 +1 |
| (with $C_8F_{17}SO_3^{\ominus}$ and $\overset{\oplus}{N}(CH_3)_3$) | 1 | −3 |
|  | 3 | −4 |
|  | 10 | −2 |
|  | 30 | 0 |
|  | 100 | −2 |

What we claim is:

1. An isopropylbenzene having the general formula:

$$\begin{array}{c} CH_3 \diagdown \diagup CH_3 \\ CH \\ \bigcirc \\ R^1-CH \\ R^2-\overset{\oplus}{N}\ R_fX^{\ominus} \\ R^3 \diagup \diagdown R^4 \end{array}$$

in which:
R$^1$=CH$_3$, R$^2$=R$^3$=R$^4$=H and R$_f$X$^-$ is C$_8$F$_{17}$SO$_3^-$,
R$^1$=R$^4$=CH$_3$, R$^2$=R$^3$=H and R$_f$X$^-$ is C$_8$F$_{17}$SO$_3^-$,
R$^1$=R$^3$=R$^4$=CH$_3$, R$^2$=H and R$_f$X$^-$ is C$_8$F$_{17}$SO$_3^-$,
R$^1$=R$^2$=R$^3$=R$^4$=CH$_3$ and R$_f$X$^-$ is C$_8$F$_{17}$SO$_3^-$,
R$^1$=R$^2$=H, R$^3$=R$^4$=CH$_3$ and R$_f$X$^-$ is C$_8$F$_{17}$SO$_3^-$,
R$^1$=R$^2$=R$^3$=H, R$^4$=CH$_3$ and R$_f$X$^-$ is C$_8$F$_{17}$SO$_3^-$,
R$^1$=CH$_3$, R$^2$=C$_2$H$_5$, R$^3$=R$^4$=H and R$_f$X$^-$ is C$_8$F$_{17}$SO$_3^-$,
R$^1$=C$_3$H$_7$, R$^2$=R$^3$=R$^4$=H and R$_f$X$^-$ is C$_5$F$_{17}$SO$_3^-$, and
R$^1$=CH$_3$, R$^2$=R$^3$=R$^4$=H and R$_f$X$^-$ is C$_5$F$_{11}$SO$_2^-$.

2. A compound according to claim 1 in which R$^1$=CH$_3$ and R$^2$=R$^3$=R$^4$=H and R$_f$X$^{\ominus}$ is C$_8$F$_{17}$SO$_3^{\ominus}$.

3. A compound according to claim 1 in which $R^1=R^4=CH_3$ and $R^2=R^3=H$ and $R_fX^\ominus$ is $C_8F_{17}SO_3^\ominus$.

4. A compound according to claim 1 in which $R^1=R^3=R^4=CH_3$ and $R^2=H$ and $R_fX^\ominus$ is $C_8F_{17}SO_3^\ominus$.

5. A compound according to claim 1 in which $R^1=R^2=R^3=R^4=CH_3$ and $R_fX^\ominus$ is $C_8F_{17}SO_3^\ominus$.

6. A compound according to claim 1 in which $R^1=R^2=H$ and $R^3=R^4=CH_3$ and $R_fX^\ominus$ is $C_8F_{17}SO_3^\ominus$.

7. A compound according to claim 1 in which $R^1=R^2=R^3=H$ and $R^4=CH_3$ and $R_fX^\ominus$ is $C_8F_{17}SO_3^\ominus$.

8. A compound according to claim 1 in which $R^1=CH_3$, $R^2=CH_2H_5$, $R^3=R^4=H$ and $R_fX^\ominus=C_8F_{17}SO_3^\ominus$.

9. A compound according to claim 1 in which $R^1=C_3H_7$, $R^2=R^3=R^4=H$ and $R_fX^\ominus=C_8F_{17}SO_3^\ominus$.

10. A compound according to claim 1 in which $R^1=CH_3$, $R^2=R^3=R^4=H$ and $R_fX^\ominus=C_5F_{11}CO_2^\ominus$.

* * * * *

UNITED STATES PATENT AND TRADEMARK OFFICE
CERTIFICATE OF CORRECTION

PATENT NO. : 4,350,644

DATED : September 21, 1982

INVENTOR(S) : John Stevens and Stephen Newman

It is certified that error appears in the above—identified patent and that said Letters Patent is hereby corrected as shown below:

Column 4, line 37, after the word "acid", delete "(50 ml)" and insert --(50 g) in ethanol (150 ml)--.

Column 6, line 66, delete "Examples 1 to 4" and insert --Examples 1 to 5--.

Column 7, lines 31 and 32, delete "surface. [new paragraph] In contact" and insert --surface in contact--.

Column 10, line 9, delete "$R^2=CH_2H_5$" and insert --$R^2=C_2H_5$--.

Signed and Sealed this

Fourteenth Day of June 1983

[SEAL]

Attest:

DONALD J. QUIGG

Attesting Officer     Acting Commissioner of Patents and Trademarks